US012642305B2

(12) United States Patent (10) Patent No.: US 12,642,305 B2

Stockall (45) Date of Patent: Jun. 2, 2026

(54) METHOD AND VAPOUR GENERATING DEVICE FOR INDICATING A DIRECTION TO AN AREA OF INTEREST

(71) Applicant: JT International SA, Geneva (CH)

(72) Inventor: Adrian Peter Stockall, Miami, FL (US)

(73) Assignee: JT International SA, Geneva (CH)

( * ) Notice: Subject to any disclaimer, the term of this patent is extended or adjusted under 35 U.S.C. 154(b) by 532 days.

(21) Appl. No.: 17/800,059

(22) PCT Filed: Feb. 11, 2021

(86) PCT No.: PCT/EP2021/053372

§ 371 (c)(1),
(2) Date: Aug. 16, 2022

(87) PCT Pub. No.: WO2021/170418

PCT Pub. Date: Sep. 2, 2021

(65) Prior Publication Data

US 2023/0076474 A1 Mar. 9, 2023

(30) Foreign Application Priority Data

Feb. 25, 2020 (EP) ..................................... 20159330

(51) Int. Cl.
*A24F 40/65* (2020.01)
*A24F 40/40* (2020.01)
(Continued)

(52) U.S. Cl.
CPC .............. *A24F 40/65* (2020.01); *A24F 40/40* (2020.01); *A24F 40/50* (2020.01); *A24F 40/60* (2020.01);
(Continued)

(58) Field of Classification Search
None
See application file for complete search history.

(56) References Cited

U.S. PATENT DOCUMENTS

| | | | | |
|---|---|---|---|---|
| 10,496,362 B2 * | 12/2019 | Li | .................. | B62D 15/0285 |
| 2010/0057344 A1 * | 3/2010 | Nezu | .................. | G01C 21/20 |
| | | | | 701/533 |

(Continued)

FOREIGN PATENT DOCUMENTS

| | | |
|---|---|---|
| CN | 109497628 A | 3/2019 |
| CN | 110167370 A | 8/2019 |

(Continued)

OTHER PUBLICATIONS

International Search Report for Application No. PCT/EP2021/053372 mailed Apr. 29, 2021, pp. 1-4.

(Continued)

*Primary Examiner* — Tamara L Weber

(74) *Attorney, Agent, or Firm* — Lerner David LLP

(57) ABSTRACT

A vapour generating device includes a vapour generating means configured to generate aerosol; a receiver configured to receive a positioning signal; a processor configured to determine a direction from a determined position of the vapour generating device to an area of interest; and an indicator configured to indicate to a user of the vapour generating device the direction to the area of interest. The vapour generating device enables a user to be guided to an area of interest such as a designated vaping area or a retail establishment selling vaping supplies.

14 Claims, 7 Drawing Sheets

(51) Int. Cl.

| | | |
|---|---|---|
| *A24F 40/50* | (2020.01) | |
| *A24F 40/60* | (2020.01) | |
| *A61M 11/04* | (2006.01) | |
| *A61M 15/06* | (2006.01) | |
| *G01C 21/20* | (2006.01) | |

(52) U.S. Cl.

CPC .......... *A61M 11/041* (2013.01); *A61M 15/06* (2013.01); *G01C 21/20* (2013.01); *A61M 2205/332* (2013.01); *A61M 2205/3592* (2013.01); *A61M 2205/505* (2013.01); *A61M 2205/581* (2013.01); *A61M 2205/582* (2013.01); *A61M 2205/583* (2013.01); *A61M 2205/587* (2013.01)

(56) References Cited

U.S. PATENT DOCUMENTS

| | | | | |
|---|---|---|---|---|
| 2013/0340775 A1* | 12/2013 | Juster | ............... | H04L 12/1827 |
| | | | | 131/273 |
| 2015/0181945 A1 | 7/2015 | Tremblay | | |
| 2015/0286324 A1 | 10/2015 | Suzuki | | |
| 2015/0327596 A1* | 11/2015 | Alarcon | .............. | H04L 67/535 |
| | | | | 131/328 |
| 2015/0330797 A1 | 11/2015 | Shukla | | |
| 2017/0302324 A1* | 10/2017 | Stanimirovic | ....... | H04M 1/185 |
| 2018/0136338 A1 | 5/2018 | Sur et al. | | |
| 2018/0242634 A1 | 8/2018 | Sur | | |
| 2018/0286208 A1 | 10/2018 | Baker et al. | | |
| 2018/0336007 A1 | 11/2018 | Li | | |
| 2019/0142071 A1 | 5/2019 | Seok | | |
| 2021/0011446 A1* | 1/2021 | Anderson | ........... | G05B 19/042 |

FOREIGN PATENT DOCUMENTS

| | | | |
|---|---|---|---|
| JP | H08184453 | A | 7/1996 |
| JP | H11230775 | A | 8/1999 |
| JP | 2001272234 | A | 10/2001 |
| JP | 2007189722 | A | 7/2007 |
| JP | 4261851 | B2 | 4/2009 |
| JP | 2019527049 | A | 9/2019 |
| KR | 20190035233 | A | 4/2019 |
| WO | 2013161416 | A1 | 10/2013 |
| WO | 2019121774 | A1 | 6/2019 |
| WO | 2019126805 | A1 | 6/2019 |

OTHER PUBLICATIONS

Mishra, Sudhir "Vaporcade Jupiter IO 3—world's first smartphone you can smoke," Techcresendo, Jan. 11, 2016 (Jan. 11, 2016), pp. 1-3, XP055720689. Retrieved from the Internet: URL:https://techcresendo.com/vaporcade-jupiter-io-3-worlds-first-smartphone-you-can-smoke/.

Search Report dated Feb. 14, 2025 from the Office Action for Chinese Application No. 202180016831.6 Issued Feb. 22, 2025, pp. 1-3.

\* cited by examiner

101

301

303

701

703

705

707

709

711

START

RECEIVING AT A RECEIVER A POSITIONING SIGNAL

DETERMINING AT A PROCESSOR A DIRECTION FROM A DETERMINED POSITION OF THE VAPOUR GENERATING DEVICE TO AN AREA OF INTEREST

INDICATING BY AN INDICATOR TO A USER OF THE VAPOUR GENERATING DEVICE THE DIRECTION TO THE AREA OF INTEREST

HAS THE USER ARRIVED AT THE AREA OF INTEREST?

NO

YES

END

METHOD AND VAPOUR GENERATING DEVICE FOR INDICATING A DIRECTION TO AN AREA OF INTEREST

CROSS-REFERENCE TO RELATED APPLICATIONS

The present application is a national phase entry under 35 U.S.C. § 371 of International Application No. PCT/EP2021/053372, filed Feb. 11, 2021, published in English, which claims priority to European Application No. 20159330.8 filed Feb. 25, 2020, the disclosures of which are incorporated herein by reference.

FIELD

The present invention relates to vapour generating devices. In particular, the use of vapour generating devices to determine a direction to a particular geographical area.

BACKGROUND

Vaping devices, such as e-cigarettes, are becoming a popular alternative to conventional cigarettes. In some countries vaping may be restricted in certain public locations in similar ways to traditional smoking. This may mean that vaping is only permitted in certain designated vaping areas.

This has led to developments to prevent vaping devices being used outside these designated vaping areas. US 2015181945 A1 and US 2018286208 A1 describe disabling or locking a vaping device when it enters an unauthorised location where vaping is not permitted.

Restrictions only permitting vaping in certain areas may typically be implemented in large cities due to the density and size of the population. However, large cities are rapidly changing environments that are constantly being developed, with new buildings, offices and businesses coming into existence. This means that the location of these designated vaping areas may be subject to change, or there may be a high turnover of new vaping areas being created.

This can provide difficulties for the person who wants to vape. They may be unaware of the location of where they are permitted to vape, or how to get to the vaping area from their current location.

If a person wanting to vape is not aware of the location or direction to a nearby vaping area they are likely to use their smartphone by using the maps application to determine the direction to the location. This can put an additional burden on the person wishing to vape such that they always need to remember to carry their smartphone, in addition to the vaping device, when they want to vape. However, in situations where they may simply be leaving a building due to restrictions around indoor smoking, they may often forget to take their smartphone with them. This means when they need to find a designated smoking area they may be unable to do so, and may have to go back into the building to retrieve their smartphone.

The above is also true for other places of interest within a city or area. For instance, the person vaping may wish to find the nearest vaping shop, such as to buy new vaping supplies.

SUMMARY OF INVENTION

According to an aspect of the invention there is provided a vapour generating device comprising: a vapour generating means configured to generate aerosol; a receiver configured to receive a positioning signal; a processor configured to determine a direction from a determined position of the vapour generating device to an area of interest; and an indicator configured to indicate to a user of the vapour generating device the direction to the area of interest.

In this way, a user (i.e. the person vaping) can find their way to a particular location. This location may be one that they wish to find (such as a shop selling vaping supplies) or one that they are required to find in order to vape (such as a designated vaping area).

This may enable a user to find the area of interest without the reliance on traditional navigational means, such as maps or mobile communication devices. This may also remove the reliance on using the user interface of a mobile communication device for directional prompts.

By determining the position of the vapour generating device through the positioning signal received from the receiver the direction to the area of interest can be communicated to the user through the indicator. This may mean that the user does not necessarily have to carry their conventional navigational means with them, or at least they do not have to waste time using it. The vapour generating device can indicate the direction to the user in an easy to understand intuitive way.

Preferably, the vapour generating device may be an e-cigarette. The skilled person would be aware that an e-cigarette, otherwise known as an electronic cigarette, may include all types of specialised vaping devices or nebulizers.

The receiver may be a GNSS receiver configured to receive a GNSS signal to determine a GNSS coordinate of the vapour generating device. This enables an accurate position of the vapour generating device to be determined.

The GNSS receiver may be a GPS, GLONASS, Galileo, BeiDou, or any other type of satellite navigation system.

Alternatively, the receiver may be any type of wireless receiver that is capable of determining a position. This may involve using a wireless network (such as GSM or Wi-FI). This may be based on network cell identification, signal strength or any other network parameter.

Preferably, the indicator is an visual indicator. This provides a visual indication that is easy for the user to understand. The visual indicator may be an LED indicator. This can also keep the power consumed by the indicator low, as LEDs typically do not require much power. This may ensure that the indicator does not drain the power of the battery of the vaping device too quickly which may be inconvenient for the user. The indicator may be updated as the user navigates towards the area of interest to provide real-time directional information to the user. Alternatively, the visual indicator may be any type of visual indicator. This may be for instance CFL or halogen lighting means.

The visual indicator may have a region for indicating a forwards direction, a region for indicating a backwards direction, a region for indicating a left direction, and a region for indicating a right direction.

Markers may be provided to indicate the direction, and/or to indicate the orientation for the user to hold the vapour generation device when navigating. Alternatively, one end of the vapour generating device may be considered to be the top of the device by convention, and the opposite end of the device may be considered to be the bottom of the device by convention, such that the user is aware of how to hold the device.

Alternatively, the direction in which the vapour generation device is held may not matter as the vapour generation device may be aware of the way in which the user is holding the device. This may be through the processor determining the orientation of the vapour generating device before displaying the indication.

The vapour generating device may comprise a compass. The compass may be capable of detecting the Earth's magnetic field. Alternatively, or in addition, the vapour generating device may comprise one or more accelerometers. The accelerometers may be capable of determining tilt information. This may provide details on how the vapour generating device is orientated, such as when it is in the user's hand. The information from the compass and the accelerometers may be used to determine how the vapour generating device is orientated such that the directional indicators point in the correct direction to the area of interest.

The visual indicator may comprise a plurality of strips, each end of the strips configured to indicate a specific direction. The strips in some arrangements may be LED strips; alternatively, they may be any type of visual indicator as outlined above. In some arrangements, the plurality of strips may be intersecting. The strips may be arranged such that they form a cross shape.

By having a cross (otherwise known as a plus) shape the user can easily recognise the direction that is being indicated. Each end of the cross may indicate a different direction to the other ends. The left end of the cross may indicate left, the right end of the cross may indicate right, the top end of the cross may indicate forwards, and the bottom end of the cross may indicate backwards. This provides navigation over the four points of a compass. These directions are with respect to user's point of view.

In some arrangements, more than one end of the visual indicator strips may be lit up at once. This may indicate that the area of interest is in a direction that is not necessarily limited to forwards, backwards, left or right. For instance, if the area of interest is forwards but on the left both the forwards and left indicator may be lit up. This may provide a precise directional indication to the user.

In other arrangements, the visual indicator may indicate the distance in a particular direction to the area of interest. For instance, the proportion of the visual indicator strip that is illuminated may indicate the distance to the area of interest. The visual indicator strips may illuminate along their length by an amount proportional to the distance to the area of interest in that direction. This may be that each end of the strips may illuminate along their length by a proportion that is dependent on the distance to the area of interest in that direction. For instance, if the area of interest is over a certain distance in that direction, the end of the strip may be fully illuminated along its length. Whereas if the area of interest is under the certain distance in that direction, the end of the strip may only be partially illuminated along its length. In some arrangements, the amount of the illumination along the length may gradually decrease as the vaping device gets closer to the area of interest. Alternatively, in some arrangements the converse may be implemented with the proportion of the length of the strip that is illuminated increasing as the vaping device gets closer to the area of interest.

Alternatively, or in addition, the visual indicator may be arranged in a circular shape. The circular shape may be a ring shape. The section of the circle that is illuminated may indicate the direction. As outlined above this may be an LED ring. In this way, a precise indication of the direction to the area of interest can be provided to the user.

The circle, or ring, may comprise a plurality of segments. Each segment may be configured to indicate a particular direction. In some instances, there may be four segments. However, in other instances, having more segments may provide an increase in precision, as the user is provided with a more precise indication of the direction. For instance, the circle may be segmented into 6, 8, 10, 12, or more segments.

Preferably, the vapour generating device further comprises a receiving unit configured to receive location information of the area of interest. In this way, location information of the area of interest can be provided to the vapour generating device. This may mean that the vaping device does not have to store long term in memory location information of the area of interest.

In addition, this may mean that that the vaping device can receive updates regarding the area of interest.

This may be important if the area of interest regularly changes, such as if the area of interest is a designated vaping area, or vaping shop. These areas may regularly move location, or close down. This ensures that the vaping device can have the most up to date information.

The receiving unit may be a Bluetooth module. In this way, the vapour generating device can connect to nearby electronic devices also having a Bluetooth module to receive the location information. This may be a user's mobile communication device. The mobile communication device may send the location information to the vapour generating device.

Alternatively, the receiving unit may be any type of wireless receiver, or a physical connection (such as a lead in form of USB cable for transferring data between the vapor generation device and user electronic devices). The location information may also be received from any type of communication system, or server. These devices may have received the location information from a database, or a directory. This may be the World Wide Web, or any other source of information.

The receiving unit may receive the location information when the user requires directional navigation to the area of interest. This may be when the method is executed to indicate to the direction of interest. This may be initiated by a user interaction upon desiring to go to the area of interest, which causes the receiving unit to receive location information of the area of interest.

Alternatively, the vapour generating device may have received the location information prior to when the user requires navigation to the area of interest. For example, the vaping generating device may receive the location information on a periodic basis. For instance, the vaping generating device may receive the location information every hour, every day, every week, every month, or any other period of time. Alternatively, the vapour generating device may download the location information every time the vapour generating device is connected to the device from which it receives the location information. Alternatively, the vapour generating device can decide by itself that it is located in a new geographical area (e.g., a new city) and needs to update location information of the area of interest, such that the vapour generating device will download the location information next time it is connected to data source. The location information of the area of interest may comprise a map of a geographical area, the map comprising locations of a plurality of areas of interest within the geographical area.

The processor may be further configured to determine which of the plurality of areas of interest is closest to the vapour generating device and determine the direction to the closest area of interest, such that the indicator indicates to the user the direction to the closest area of interest.

There may be numerous areas of interest in a certain geographical area. This ensures that the user is directed to the one that is closest to them. Advantageously, this saves the user time in reaching their destination. In addition, it reduces the power drain on the battery of the vapour generating device as the user will be using the directional function for a shorter period of time.

Alternatively, other criteria may be used to determine which of the areas of interest to direct the user to. For instance, the criteria may be a particular type of area of interest, e.g. a vaping shop or a designated vaping area. The criteria may also include the area of interest which is determined as easiest to navigate to. This may involve requiring the user to make the smallest number of directional turns, or cross the least number of roads.

The area of interest may be a designated vaping area or a retail establishment. Alternatively, the area of interest may be any other type of area that a user may want to navigate towards.

The vapour generating device may be for vaping tobacco or tobacco substitute products. It may be either a liquid vaporiser or a heated tobacco type electronic cigarette (such as heat not burn type device). Alternatively, it may be any other type of device for producing aerosol, such as an inhaler for medical purposes.

According to a further aspect, there is provided a method performed on a vapour generating device of indicating a direction to an area of interest, the method comprising: receiving at a receiver a positioning signal; determining at a processor a direction from a determined position of the vapour generating device to an area of interest; and indicating by an indicator to a user of the vapour generating device the direction to the area of interest.

Preferably, the vapour generating device may be an e-cigarette.

Preferably, the method further comprises repeating the steps of receiving, determining and indicating, such that the indication is updated as the user navigates towards the area of interest.

The method may comprise performing the receiving, determining and indicating repeatedly at fixed points in time. Alternatively, or in addition, the determining and/or indicating steps may be repeated when it is determined that the vapour generating device is at a specific position. For instance, it may be determined that the vapour generating device is at a location where there are multiple routes to take (such as a cross road). This may be a criteria that causes the indicator to be updated.

In this way, the direction to the area of interest can be updated at periodic intervals. This ensures that as the user navigates towards the area of interest the indicator provides updated directional prompts to the user. This can be used to ensure that at a particular moment in time the user is provided with a directional indicator based on their current position.

These fixed points in time may be every second, every 10 seconds, every 30 seconds, every minute, every five minutes, or any other time period. This time interval may be based on specific parameters, such a user's typical walking speed, or a distance to the area of interest.

According to a further aspect, there is provided a computer program product comprising instructions which, when the program is executed by a computer, cause the computer to carry out the method of the aspect described above.

According to a further aspect there is provided a computer readable storage medium comprising instructions which, when executed by a computer, cause the computer to carry out the method of the aspect described above.

DETAILED DESCRIPTION

Figure 1:
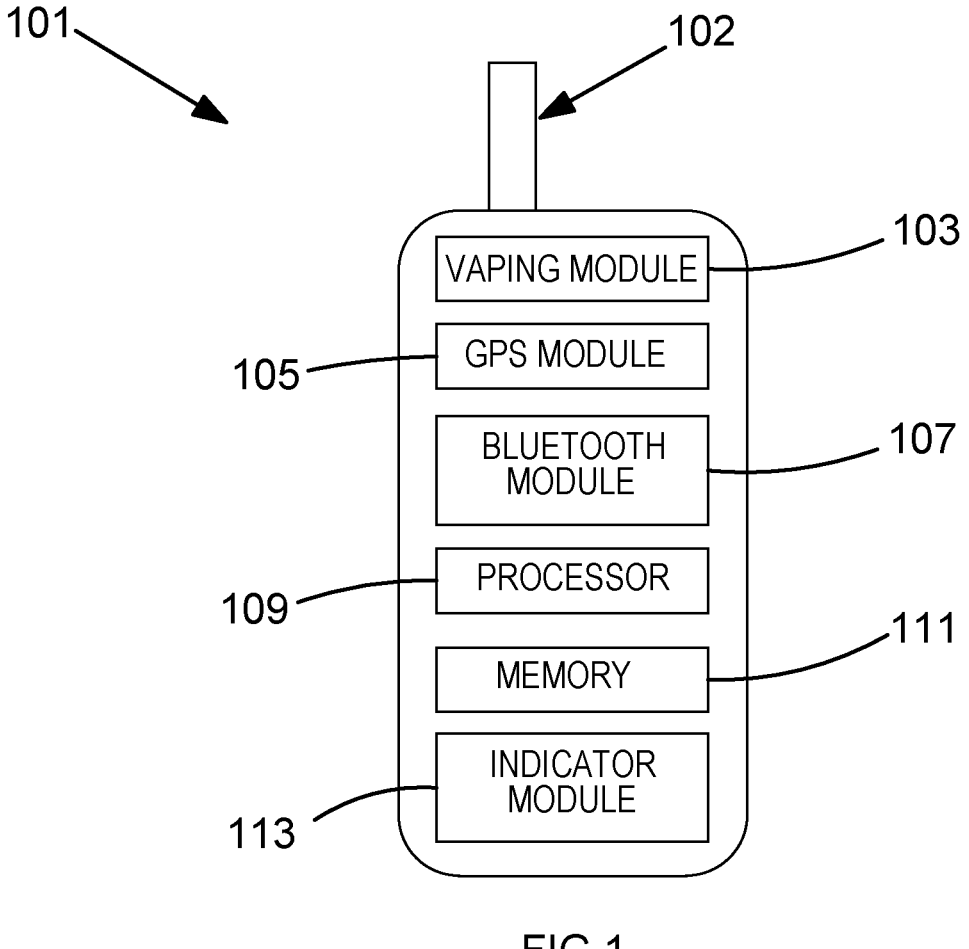
FIG. 1 shows a schematic internal view of a vapour generating device according to the invention.

FIG. 1 shows a schematic internal view of a vapour generating device 101 according to the invention. The vapour generating device 101 is for vaping tobacco or tobacco substitute products, otherwise known as an electronic-cigarette or e-cigarettes.

The vapour generating device 101 is configured to produce an aerosol. The vapour generating device can be either a liquid vaporiser or a heated tobacco type electronic cigarette (such as heat not burn type device).

These may be provided as a consumable to be used as an attachment to a liquid vaporizer by enhancing vapour with a flavour or a substance (such as nicotine). Typically, the flavour enhancement is provided as a consumable in the form of a flavoured filter. The filter can also be provided without flavour and can be configured to remove larger vapour droplets and projections from the vapour. Alternatively, the consumable can be a tobacco rod comprising an aerosol-forming substance such as propylene glycol or glycerin and configured to release a vapour when heated, i.e. a so called "heat-stick".

Alternatively, the vapour generating device may comprise a reservoir configured to be filled with the vaporisable material. This may be a vaporisable liquid such as the aerosol forming substances described above, such as an e-liquid.

Alternatively, the vaporisable material put into the reservoir may be tobacco extract.

Vapour generating device 101 comprises vaping module 103. The vaping module 103 is responsible for controlling the production of vapour. This may control an atomizer (not shown) which heats the vaporisable material to form aerosol. The vapour generating device 101 has mouthpiece 102 through which a user puffs to inhale the aerosol.

The vapour generating device also comprises a GPS module 105, a Bluetooth module 107 and an indicator module 113.

The control of each of the modules is provided by processor 109 in conjunction with memory 111 which are present in the vapour generating device 101.

GPS module 105 is configured to determine the GPS location of the vapour generating device 101. This can be used to determine the exact position of the vapour generating device 101 for use in providing directions to a particular location.

Bluetooth module 107 enables the vapour generating device 101 to connect to other devices which have Bluetooth capabilities. By forming a Bluetooth connection mapping information can be downloaded to the vapour generating device 101. This mapping information may be stored in the memory 111 of the vapour generating device 101. The mapping information includes details of nearby vaping areas where vaping is permitted. The mapping information may be stored in the memory 111 in either long term or short term memory depending on when the mapping information is received by the vapour generating device 101.

The processor 109 is configured to determine the current position of the vapour generating device 101 using the GPS coordinates provide by the GPS module 105. The processor 109 can then determine the direction from the current location of the vapour generating device 101 to a nearby vaping area using the mapping information. The processor 111 then instructs the indicator module 113 to control an indicator to display the direction from the current location of the vapour generating device 101 to a nearby vaping area.

Figure 2:
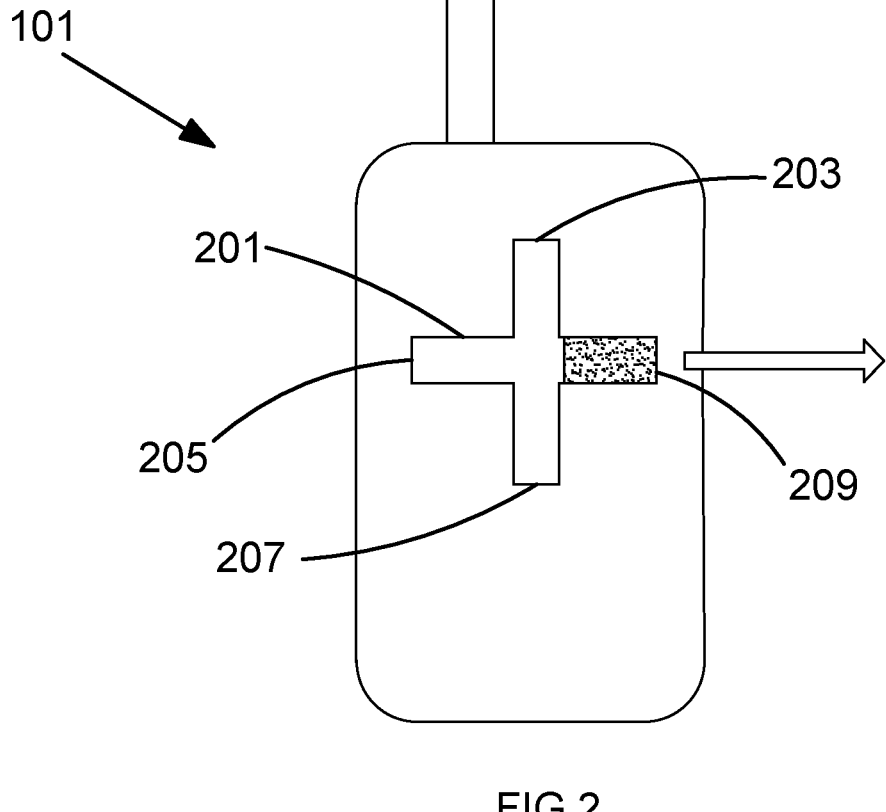
FIG. 2 shows a schematic external view of a vapour generating device according to the invention illustrating an indicator according to a first embodiment.

FIG. 2 shows a schematic external view of a vapour generating device 101 according to the present invention. The vapour generating device 101 comprises a cross shaped LED indictor 201. The cross shaped LED indicator 201 has four ends 203 205 207 209. Each end 203 205 207 209 of the cross of the LED indicator 201 indicates a different direction to the user.

When indicator 201 is viewed by a user in the orientation shown in FIG. 2 the end 203 indicates "go forwards", end 207 indicates "go backwards", end 205 indicates "go left", and end 209 indicates "go right".

End 209 of indicator 201 is currently illuminated in the arrangement shown in FIG. 2. This is currently indicating for the user to go right. More than a single end of the LED indicator 201 may be illuminated at any one time. For instance, if the vaping area is in front but on the right then both ends 203 and 209 may be illuminated to indicate this to the user. Alternatively, if the vaping area is behind but on the left both ends 205 and 207 may be illuminated at once.

Figure 3:
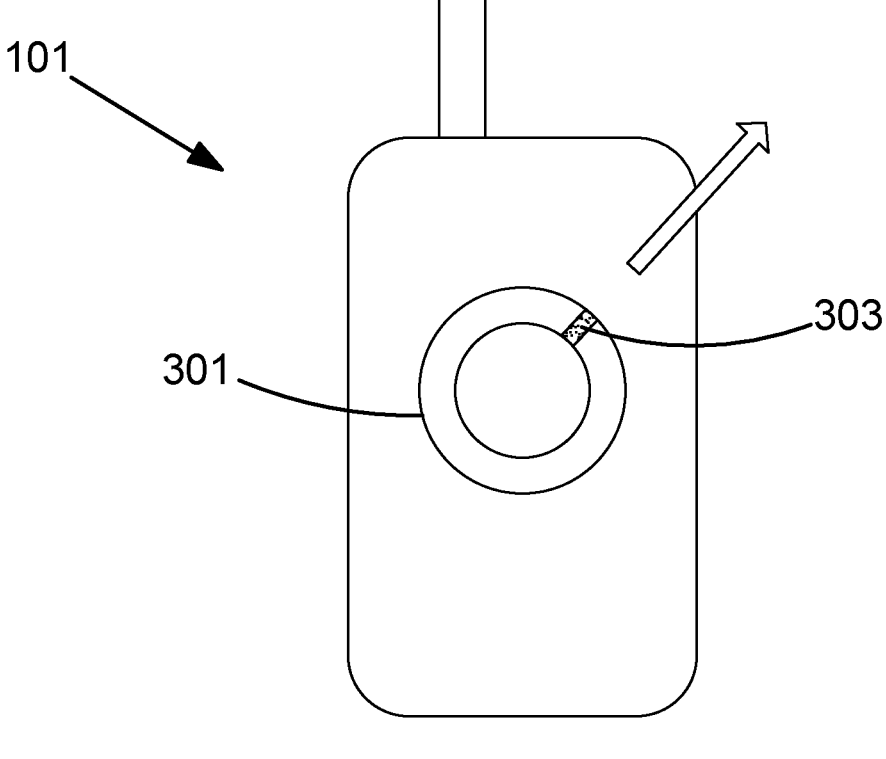
FIG. 3 shows a schematic external view of a vapour generating device according to the invention illustrating an indicator according to a second embodiment.

FIG. 3 shows a schematic external view of a vapour generating device 101 according to the present invention showing a different indicator 301 to the indicator 201 shown in FIG. 2. The indicator in FIG. 3 is a ring shaped LED indicator 301. The ring shaped LED indicator 301 is divided into individual segments around the circumference of the ring. Each of these segments indicates a particular direction. One such segment 303 is shown illuminated in FIG. 3. The segment 303 is illuminated to indicate the direction to the vaping area from the present location of the vapour generating device 101. In this arrangement shown in FIG. 3 this is approximately forwards and on the right when viewed from the point of view shown in FIG. 3. By having many segments this may provide a more precise way of indicating a direction to a user than using the indicator 201 shown in FIG. 2.

When the user has arrived at the desired location the LED indicator may indicate to the user that they have arrived at the destination. This may be through illuminating the whole of the LED indicator. Alternatively, it may be through the LED indicator switching off. Or a different type of indication may be used, such as a sound or a haptic indicator.

The vapour generation device 101 further includes a compass and one or more accelerometers (not shown). These ensure that the orientation of the vapour generating device

101 can be determined so that the indicators 201 301 adjust in response to the movement of the user and point the user in the correct direction. Specifically, the compass can determine the directional information regarding where the vapour generation device 101 is pointing, with the accelerometers for determining tilt information.

Figure 4:
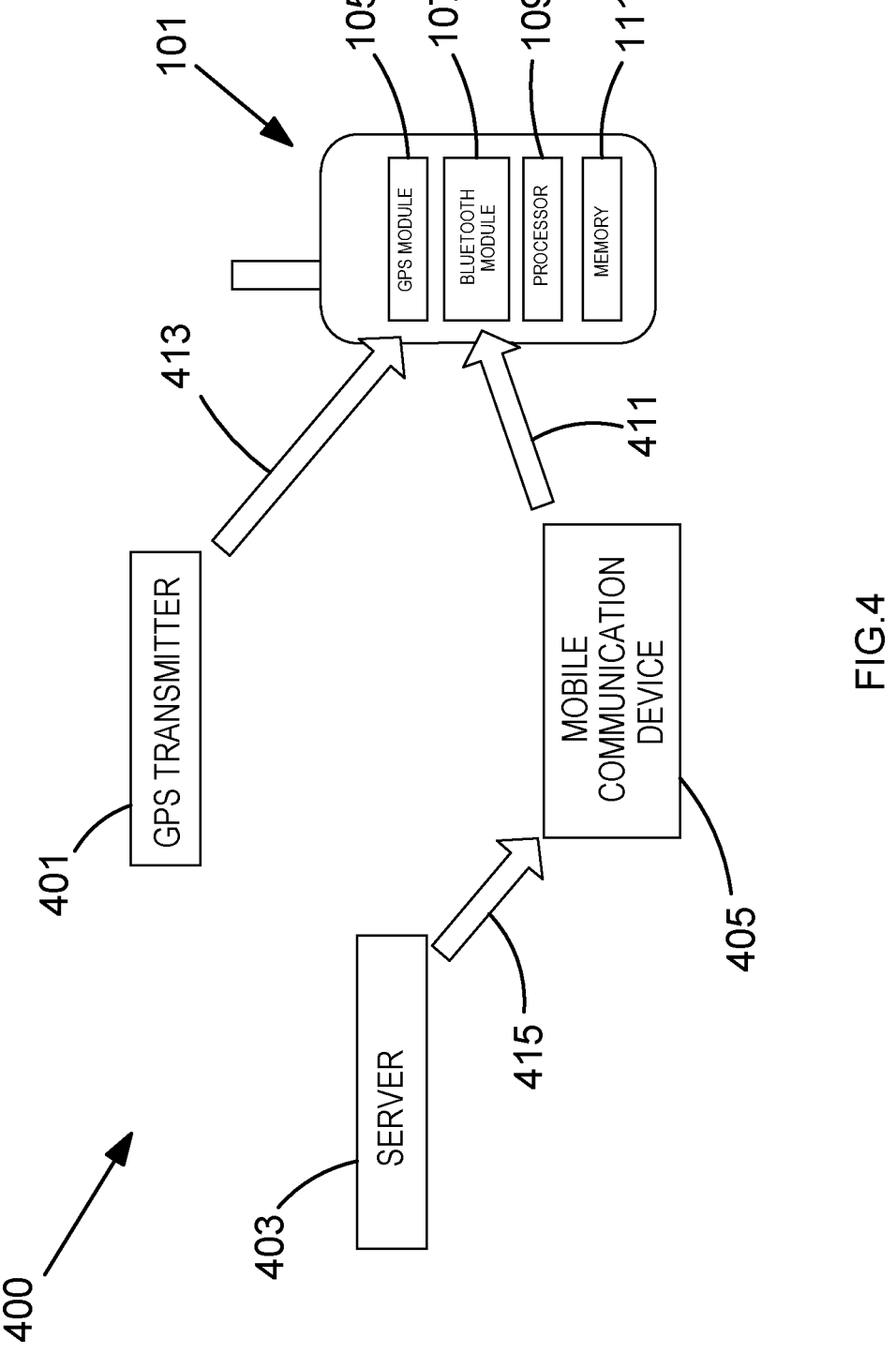
FIG. 4 shows a schematic view of a system for enabling geographical navigation using a vapour generating device.

FIG. 4 shows a schematic view of a system 400 for enabling geographical navigation using the vapour generating device 101 according to the present invention. The system 400 includes vapour generation device 101 as shown in FIG. 1. This vapour generation device 101 may have an indicator as shown in FIG. 2 or 3, or any other type of indicator suitable for indicating a direction to a user (note that the indicator module is not explicitly shown in FIG. 4).

GPS module 105 of the vapour generating device 101 receives GPS signals 413 from GPS satellites represented by GPS transmitter 401 in FIG. 4. The GPS signals are used by the processor 109 of the vapour generating device 101 to determine the current location of the vapour generating device 101. This may be instigated periodically, or upon a trigger caused by the user when they wish to find the direction to a vaping area.

Bluetooth module 107 establishes a Bluetooth connection 411 with mobile communication device 405. The vapour generating device 101 can then receive mapping information, which includes details of the locations of one or more vaping areas, from the mobile communication device 405. The location information can then be used by processor 109 to determine the direction from the current location of the vapour generation device 101 (obtained through using the GPS coordinates) to the vaping area.

The mobile communication device 405 may be the user's smartphone. As shown in FIG. 4 the mobile communication device 405 receives the mapping information from a server 203. The server 403 is a central repository which stores details of all of the vaping areas for a certain geographical area. For instance, it may store mapping information containing details of all of the vaping areas in a particular city. The mobile communication device communicates with the server through wireless radio signals 415 (such as Wi-FI, 5G, 4G, 3G etc.) to download the mapping information.

A procedure of how the vapour generating device 101 may be used to direct a user to a particular vaping area according to the present invention will now be discussed.

When the user wishes to vape the navigation process is started. This may be user initiated. For instance it may be through activating a specific button on the vapour generating device 101, or through a gesture such as the user shaking the vapour generating device. Alternatively, it may be automatically initiated by the vapour generating device. This may include the vapour generating device determining that the user is attempting to vape in a location that is not permitted. Rather than causing the heating device to switch on these cause the GPS module 105 to obtain the GPS coordinates of the current position of the vapour generating device 101 and the processor to determine the current location of the vapour generating device 101.

The processor 109 then determines the direction to the vaping area based on mapping information stored in memory 111 that has previously been received at the vaping device 101.

The processor 109 then instructs the indicator module 113 to cause the indicator 201 301 to display directional indicators to the vaping area. The user can then follow the directional indicator to navigate to the vaping area.

Throughout the navigation of the user to the vaping area the processor 109 continually determines the updated location of the vapour generating device 101. This is then used throughout the navigation to determine a continually updated direction from the current location to the destination vaping area. The indicator 201 301 displays the continually updated direction based on the most recent position of the vapour generating device 101 that has been determined. In this way, the updating of the directional indicator may be triggered based on the current GPS coordinate of the vapour generating device 101. For instance, a change in the GPS coordinate of the vapour generating device may cause the indicator to be updated. Alternatively, or in addition, the updating of the indicator may be done periodically. The updating of the directional indicator may be every second, every 10 seconds, every 30 seconds, every minute, every five minutes, or any other time period. This may be based on specific parameters, such a user's typical walking speed, or a distance to the vaping area.

Once the user reaches the destined vaping area the process will then stop with the indicator indicating to the user that they have arrived at the destination. This may be through the indicator flashing, through the indicator turning off, or any other type of indication as discussed herein.

As outlined above the vapour generating device 101 has stored in its memory 111 mapping information relating to a geographical area. Preferably, the vapour generating device 101 has obtained the mapping information from the mobile communication device 405 at an earlier point in time before the user wishes to use the vapour generating device 101 for navigation. Thus, the navigation can be performed using the vapour generating device 101 even when not in close proximity to the mobile communication device 405, such as when the user is not carrying their mobile communication device 405.

The vapour generating device 101 may download the mapping information over the Bluetooth connection 411 periodically. This may be at periodic intervals, such as every day, every week, or every month. This can be selected dependent on how often the vaping areas are likely to change. The user may pre-select a specific geographical area in which they are likely to be in. This may be the city that they live in, or a specific area thereof. Alternatively, if they are visiting a specific location that they have not previously visited they may download the mapping information for that area before visiting the area.

Alternatively, if the mapping information has not been downloaded to the vapour generating device 101 before visiting a particular location, once arrived, the vapour generating device 101 can determine by itself that it is located in a new geographical area and that it needs to update the mapping information stored in memory.

In this regard, the vapour generating device can send a request to the mobile communication device 405 (e.g., a paired smartphone) over the Bluetooth connection 411 to download new mapping information. The mobile communication device 405 then sends the mapping information for this new location to the vapour generating device. The vapour generating device can then store this updated mapping information in its memory. The processor of the vapour generating device may decide whether to replace the existing mapping information with this newly received mapping information or to store this new mapping information in addition to the previously stored mapping information.

Although it is discussed above that the navigation process may be instigated through actions related the vapour generating device 101 it instead may be instigated through actions performed on or by the mobile communication device 405.

The user may have software on their mobile communication device 405, such as their smartphone, which includes functionality for directing the user to a vaping area using the vapour generating device 101 as shown in FIGS. 1 to 4. The user wanting to vape causes the software application, otherwise known as an app, to execute on their mobile communication device 405.

The mobile communication device 405 is then paired with the vapour generation device 101 through the Bluetooth connection 411. The vapour generation device 101 may already have been paired with the mobile communication device 405, or they may be paired at the moment when the user wishes to vape.

The execution of the software on the mobile communication device 405 causes mapping information to be sent from the mobile communication device 405 to the vapour generating device 101 through the Bluetooth connection 411. The mapping information relates to a certain geographical region which may be selected by the user through a user interface of the mobile communication device 405. Alternatively, it may be automatically selected by the mobile communication device based on the current location of the user. The current location of the user may have been determined be the mobile communication device based on the GPS signal 413 received by the vaping device or its own positioning means (through GNSS or radio signals). The mobile communication device 405 will have received the mapping information from a server 403 as discussed above.

The mobile communication device 405 signals the vapour generating device 101 through the Bluetooth connection 411 to determine its current position. The GPS module 105 obtains the GPS coordinates of the current position of the vapour generating device 101, which are used by the processor 109 to determine its current position. The processor 109 then determines the direction to a vaping area based on the current position and the mapping information.

The direction is then indicated to the user through indicators 201 203 as described above, and is updated throughout the user's navigation to the vaping area as described above.

Figure 5:
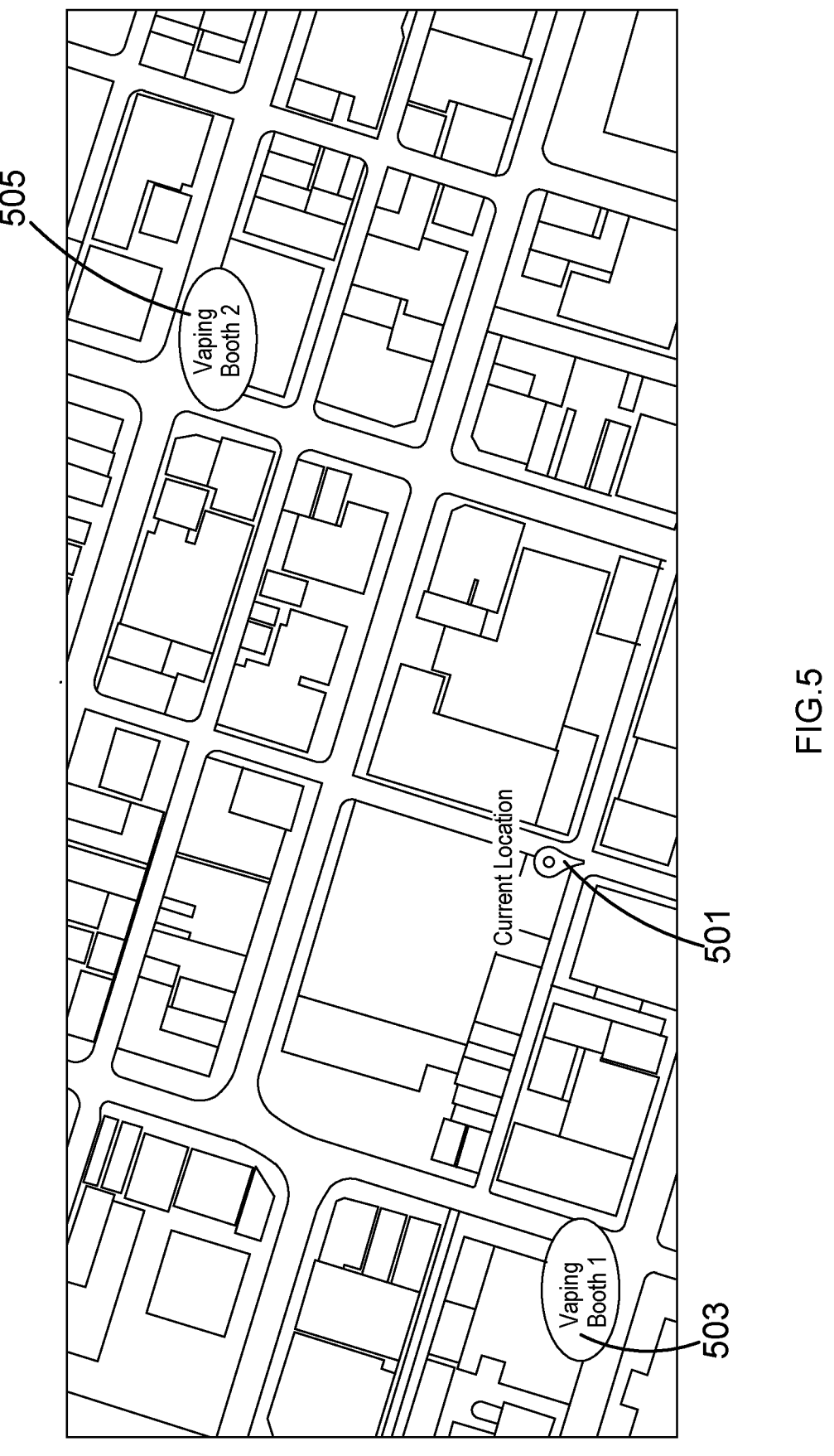
FIG. 5 shows a map of a geographical area showing vaping booths and a user's current location.

FIG. 5 shows a map of a geographical location which represents the mapping information that may be provided to the vapour generating device 101 from the mobile communication device. The current position 501 of the vapour generating device 101 is shown for clarity, as the current position 501 is not provided by the mapping information and is instead determined by the mobile communication device 101 through GPS module 105.

Two vaping areas vaping booth 503 and vaping booth 505 are shown. These are designated vaping areas at which, by law, vaping is permitted. These are provided in the mapping information received at the vapour generating device 101. The processor of the vapour generating device 101 is configured to determine the direction from the current location to one of the vaping areas 503 505.

As can be seen from FIG. 5 the mapping information may include multiple vaping areas 503, 505. The processor of the vapour generating device is configured to select one of the vaping areas 503 505 to direct the user towards. This may be determined based on which of the vaping areas is closest to the current location of the vapour generating device 101. This may be the exact distance between the two locations or the distance of the route that a user would take when walking between the two locations. However, other criteria may be used. The criteria may include the area of interest which is determined as easiest to navigate to. This may involve requiring the user to make the smallest number of directional turns, or cross the least number of roads as pre-setting rules. The user may input the pre-setting rules through an interface on electronic devices (e.g., smartphone phone) and the pre-setting rules can be transmitted from the electronic device to vapour generating device when they are connected.

Figures 6A, 6B:
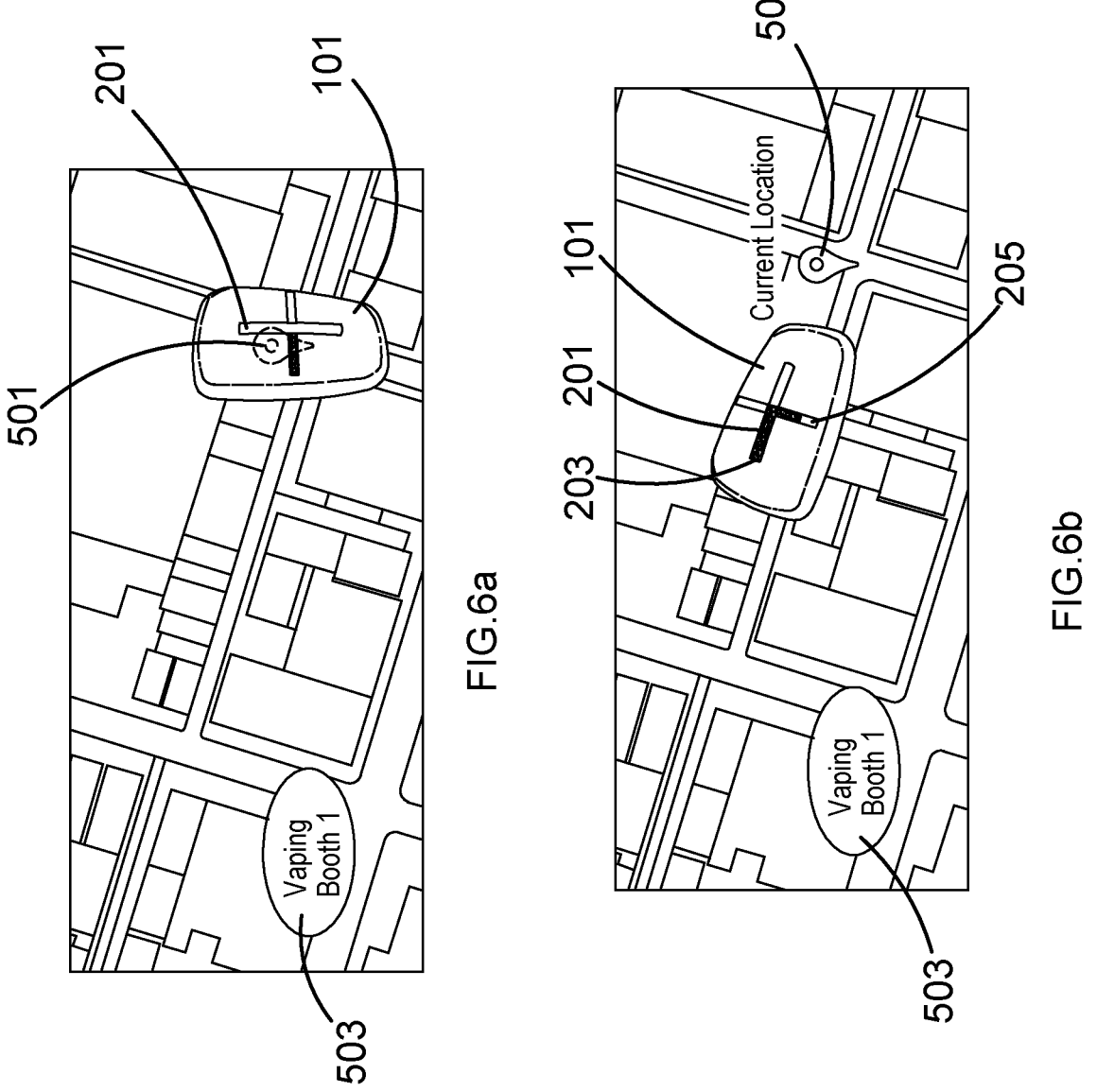
FIGS. 6a and 6b show a map of a geographical area showing a vaping device navigating to a vaping booth.

FIGS. 6*a* and 6*b* shows the vapour generating device navigating from the current location 501 shown in FIG. 5 to the vaping area 503.

In FIG. 6*a* the vapour generating device is currently at the starting location 501. The indicator 201 indicates that the destination vaping area 503 is on the left with respect to the current orientation of the vapour generating device 101 when viewed from the position shown in FIG. 6*a*.

FIG. 6*b* shows the user navigating from the starting location 501 towards the destination vaping area 503. The user has now started to navigate in the direction indicated by the indicator 201 shown in FIG. 6*a*. The indicator in FIG. 6*b* has now updated based on the current direction to the vaping area 503, and the current orientation of the vapour generating device 101. As can be seen the indicator 201 indicates that the vaping area is forwards and on the left. This is indicated through both ends 203 and 205 being illuminated. The indicator updates until the user arrives at vaping area 503.

Figure 7:
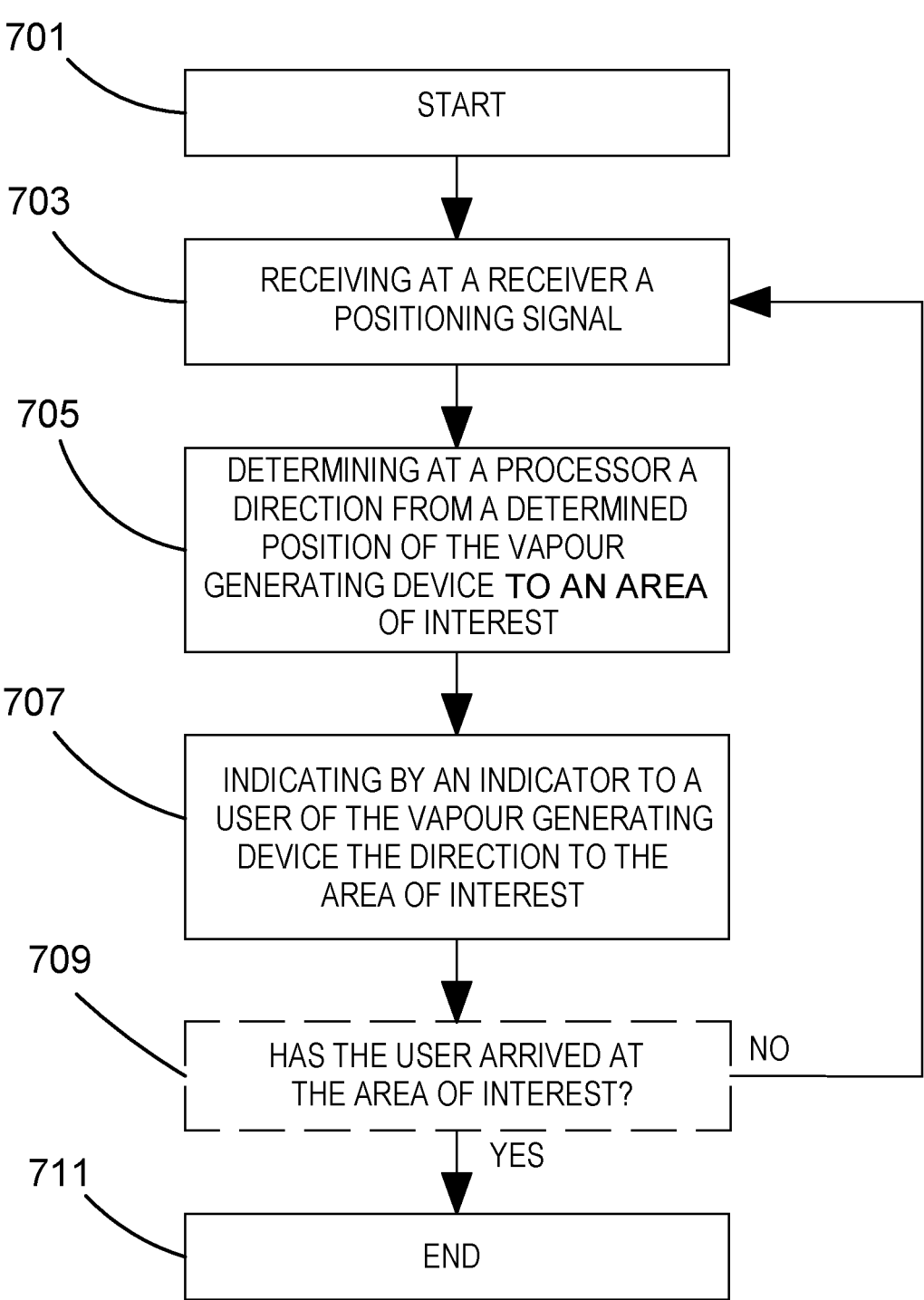
FIG. 7 shows a method performed on a vapour generating device of indicating a direction to an area of interest.

FIG. 7 is a flow chart indicating a method performed on vapour generating device 101 of indicating a direction to an area of interest.

The method starts at step 701.

At step 703 the vapour generating device receives, at a receiver of the vapour generating device, a positioning signal. This may be at a GPS module as explained above.

Step 705 involves determining at a processor of the vapour generating device a direction from a determined position of the vapour generating device to an area of interest.

Step 707 involves indicating by an indicator to a user of the vapour generating device the direction to the area of interest.

At step 709 optionally it is determined if the user has arrived at the area of interest. If the user has arrived at the area of interest the process ends at step 711.

Optionally, if the user has not arrived at the area of interest steps 703 to 707 are then repeated until the user has arrived at the area of interest, or until they stop the process. This provides updated directional indicators to the user.

The figures above have been described with respect to navigation to a designated vaping area. However, the vapour generating device may be used to navigate to any area of interest to a user. For instance, the user may realise that they have run out of vaping supplies and need to go to a vaping store. The vapour generating device may be used to navigate the user to a specific vaping store.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

Although it has been discussed above that the vapour generating device contains both a GPS module and a Bluetooth module this is not necessarily the case. The Bluetooth module may be any type of wireless module. For instance, the mapping information may be received using a WI-FI or NFC connection. Alternatively, the vapour generating device may have a radio receiver capable of receiving data over a typical telecommunication network (such as 3G, 4G, 5G, etc.). In other arrangements the vapour generating device may download the mapping information over a wired connection. A physical cable, such as USB connection may be received in a port of the vapour generating device to download the mapping information to the vapour generating device.

Alternatively, the vapour generating device rather than receiving the mapping information from the mobile communication device may instead receive the mapping information direct from the server. For instance, the vapour generating device may connect directly with the server. This may be using any of the connection types discussed above. Alternatively, the mapping information may be pre-loaded on the vapour generating device. Thus, the Bluetooth module may not necessary be required.

The GPS module may instead be any type of GNSS receiver. For instance it may be GLONASS, Galileo, Bei-Dou, or any other type of satellite navigation system.

Alternatively, the GPS module may be any type of wireless receiver that is capable of determining a position. This may involve using a wireless network (such as GSM or Wi-FI). This may be based on network cell identification, signal strength or any other network parameter. Alternatively, the GPS module may not be present. The vapour generating device may instead receive the position of the vapour generating device from the mobile communication device, for instance over the Bluetooth connection, with the position of the mobile communication device assumed to be the same as the mobile device.

The indicator is also not limited to those shown in FIGS. 2 and 3. The indicator 301 shown in FIG. 3 may have a plurality of segments each indicating a different direction. In some instances, there may be four segments. However, in other instances, having more segments may provide an increase in precision, as the user is provided with a more precise indication of the direction. For instance, the circle may be segmented into 6, 8, 10, 12, or more segments.

In addition, rather than a ring shape the indicator 301 may be a full circle without a central region with no LEDs. The circle indicator may have segments which indicate a direction each of which extend from a central point of the circle. Alternatively, the indictor may be any type of shape that can communicate a direction to a user.

The LED indicator may be of a single colour. Alternatively, the LED indicator may be composed of a plurality of colours. For instance, each of the directions may be indicated by a different colour to each other. The indicator in FIG. 2 may have end 203 a different colour to end 205, each of which also has a different colour to end 207, and each of which also has a different colour to end 209. This may aid the user in distinguishing the different directions quickly.

Alternatively, the indicator may be a different type of indicator. For instance, it may be haptic, audial or another type of visual indicator. The audial or haptic indicators may be particularly important for users who have visual impairment. The haptic feedback may be through a vibration module. The vibration module provides vibration to the user with the type of vibration indicating a different direction to the user. For instance, the length or intensity of the vibration may indicate the direction to the user. Alternatively, the audial vibration may include different sounds which indicate a specific direction to the user. Any combination of these feedback types may be used.

The above embodiments also describe the use of a compass and accelerometers to determine the orientation of the vapour generating device. These are not essential components and any alternative method of ensuring the correct direction is indicated to the user may be used. For instance, if the user always holds the vapour generating device in a specific orientation, such as flat in their palm, the tilt information of the vapour generation device does not need to be taken into consideration.

The vapour generating device need not be specifically an electronic cigarette, and it may be any type of vapour generating device. For instance, it may be a vapour generating device for medical usage. For example, an inhaler for asthma or other respiratory diseases. In this case the vapour generating device may be configured to navigate the user to a medical point of interest. This may be to navigate to a pharmacy, such as when their vapour generating device has run out of dosage. Alternatively, it may be navigate to a hospital or doctor surgery, such as if the user becomes unwell.

Each end of the LED indicator 201 shown in FIG. 2 as described above indicates a particular direction to the user by illuminating from the centre of the indicator to the end of the indicator. Alternatively, the length of each of the LEDs illuminated may signify the distance to the area of interest in that direction. For instance, if the area of interest is over a certain distance the indicator may illuminate down its full length as shown in FIG. 2. However, if the distance to the area of interest is less than a certain distance the indicator may illuminate only down a portion of the length of the indicator.

Although the mapping information received from the mobile communication device is described as indicating various designated vaping areas, the mapping information may alternatively provide details of only a single vaping area. Although this mapping information is shown as a map in FIG. 5 the information provided by the mobile communication device (or server) may instead be coordinates of the area of interest. For instance, the map may already be stored on the vapour generating device. Alternatively, the mobile device may send prompts to the vapour generating device to indicate the direction for the indicator to display to the user. This is instead of the vapour generating device carrying out the determination of the direction itself.

The invention claimed is:

1. A vapour generating device comprising:
a vapour generating means configured to generate aerosol;
a receiver configured to receive a positioning signal;
a processor configured to:
    determine, based on the positioning signal, a position of the vapour generating device;
    determine a navigational instruction from the determined position of the vapour generating device to an area of interest; and
an indicator module configured to provide the navigational instruction, wherein the navigational instruction includes a directional indication,
wherein the vapour generating device is an e-cigarette.

2. The vapour generating device of claim 1, wherein the receiver is a GNSS receiver configured to receive a GNSS signal to determine a GNSS coordinate of the vapour generating device.

3. The vapour generating device of claim 1, wherein the directional indication is a visual indicator.

4. The vapour generating device of claim 1, wherein the indicator module has a region for indicating a forward direction, a region for indicating a backwards direction, a region for indicating a left direction, and a region for indicating a right direction.

5. The vapour generating device of claim 1, wherein the indicator module comprises a plurality of LED strips each having an end configured to indicate a specific direction.

6. The vapour generating device of claim 5, wherein the plurality of LED strips are arranged to form a cross shape.

7. The vapour generating device of claim 1, wherein the indicator module is arranged in a circular shape.

8. The vapour generating device of claim 1, further comprising a receiving unit configured to receive location information of the area of interest.

9. The vapour generating device of claim 8, wherein the receiving unit is a Bluetooth module.

10. The vapour generating device of claim 8, wherein the location information of the area of interest comprises a map of a geographical area, the map comprising locations of a plurality of areas of interest within the geographical area.

11. The vapour generating device of claim 10, wherein the processor is further configured to determine which of the plurality of areas of interest is closest to the vapour generating device and determine a direction to a closest of the plurality of areas of interest, such that the indicator module indicates the direction to the closest of the plurality of areas of interest.

12. The vapour generating device of claim 1, wherein the area of interest is a designated vaping area or a retail establishment.

13. A method performed on a vapour generating device of indicating a direction to an area of interest, wherein the vapour generating device is an e-cigarette, the method comprising:
    receiving, by a receiver, a positioning signal;
    determining, by one or more processors, based on the positioning signal, a position of the vapour generating device;
    determining, by one or more processors, a direction from the determined position of the vapour generating device to an area of interest; and
    providing, by the one or more processors via an indicator module of the vapour generating device, the navigational instructions, wherein the navigational instructions includes a directional indication.

14. The method of claim 13, further comprising repeating the steps of receiving, determining and providing, such that the directional indication is updated as the vapour generating device navigates towards the area of interest.

* * * * *